United States Patent [19]
Goodwin et al.

[11] Patent Number: 6,117,674
[45] Date of Patent: *Sep. 12, 2000

[54] PATHOGEN PROPAGATION IN CULTURED THREE-DIMENSIONAL TISSUE MASS

[75] Inventors: Thomas J. Goodwin; Glenn F. Spaulding; David A. Wolf, all of Houston, Tex.

[73] Assignee: The United States of America as represented by the Administrator of the National Aeronautics and Space Administration, Washington, D.C.

[*] Notice: This patent is subject to a terminal disclaimer.

[21] Appl. No.: 08/366,065

[22] Filed: Dec. 29, 1994

Related U.S. Application Data

[63] Continuation-in-part of application No. 08/066,292, May 25, 1993, Pat. No. 5,496,722, which is a continuation-in-part of application No. 07/939,791, Sep. 3, 1992, Pat. No. 5,308,764, which is a continuation of application No. 07/317,921, Mar. 2, 1989, Pat. No. 5,007,497, which is a continuation-in-part of application No. 07/317,776, Mar. 2, 1989, Pat. No. 5,155,034, and a continuation of application No. 07/213,558, Jun. 30, 1988, Pat. No. 5,026,650, and a continuation-in-part of application No. 07/625,345, Dec. 11, 1990, Pat. No. 5,153,131.

[51] Int. Cl.[7] ..................................................... C12N 5/00
[52] U.S. Cl. ...................... 435/325; 435/235.1; 435/366; 435/383
[58] Field of Search ............................... 435/240.24, 366, 435/383, 325, 235.1

[56] References Cited

U.S. PATENT DOCUMENTS

| | | | |
|---|---|---|---|
| 4,164,566 | 8/1979 | Provost et al. | 424/89 |
| 4,203,801 | 5/1980 | Telling et al. | 435/284 |
| 4,352,887 | 10/1982 | Reid et al. | |
| 4,721,675 | 1/1988 | Chan et al. | 435/239 |
| 4,940,853 | 7/1990 | Vandenburgh | |
| 4,963,489 | 10/1990 | Naughton et al. | |
| 4,988,623 | 1/1991 | Schwarz et al. | 435/286 |
| 5,026,637 | 6/1991 | Soule et al. | 435/29 |
| 5,026,650 | 6/1991 | Schwarz et al. | 435/286 |
| 5,032,508 | 7/1991 | Naughton et al. | 435/32 |
| 5,153,131 | 10/1992 | Wolf et al. | |
| 5,155,034 | 10/1992 | Wolf et al. | |

OTHER PUBLICATIONS

"Defining Conditions to Promote the Attachment of Adult Human Colonic Epithelial Cells", Michel Buset, Sidney Wanawer & Eileen Friedman, In Vitro Cell & Dev. Biol., vol. 23, #6, pp 403–412 (Jun. 1987).

"Colon Organ Culture as a Model for Carcinogenesis", Abulkalam M. Shamsuddin, Colon Cancer Cells, Moyer and Poste, Eds. Academic Press, Inc., pp. 137–153, 1990.

"Culturing Hepatocytes and Other Differentiated Cells", Lola M. Reid and Douglas M. Jefferson, Hepatology, vol. 4 #3, pp. 548–559 (1984).

"Retention of Differentiated Characteristics in Human Fetal Keratinocytes in Vitro", Anne R. Haake and Alfred T. Lane, In Vitro Cellular & Development Biology, vol. 25 #7, pp. 592–600, Jul. 1989.

"Clonal Growth of Human Prostatic Epithelial Cells is Stimulated by Fibroblasts", John N. Kabalin, Donna M. Peehl & Thomas A. Stamey, The Prostate, vol. 14, pp. 251–263, 1989.

"Epidemiology of Norwalk Gastroenteritis and the Role of Norwalk Virus in Outbreaks of Acute Nonbacterial Gastroenteritis", Jonathan E. Kaplan, et al, Annals of Internal Medicine, vol. 96 (Part 1), pp. 756–761, 1982.

"Novel Agents of Viral Enteritis in Humans", Raphael Dolin, John J. Treanor & H. Paul Madore, The Journal of Infectious Diseases, vol. 155, #3, pp. 365–376, Mar. 1987.

"Acute Infectious Nonbacterial Gastroenteritis: Etiology and Pathogenesis", Blacklow et al. Annals of Internal Medicine, 76:933–1008, 1972.

"Methods for Propagation and Characterization of Human GI and Other Cells for HIV ", Mary Pat Moyer, J. Tiss. Cult. Meth., vol. 13, pp. 107–116, 1991.

"Detection of Norwalk Antibodies and Antigen with a Biotin–Avidin Immunoassay", G. William Gary, Jr. et al, Journal of Clinical Microbiology, vol. 22, #2, pp. 274–278, 1985.

"Multiple–Challenge Study of Host Susceptibility to Norwalk Gastroenteritis in US Adults", Philip C. Johnson, et al, J. Infect. Diseases, pp. 18–21, 1990.

"Detection of non–A, non–B hepatitis antigen by immunocytochemical staining", Kenneth H. Burk et al, Proc. Natl. Acad. Sci., vol. 81, pp. 3195–3199, 1984.

Primary Examiner—Leon B. Lankford, Jr.
Attorney, Agent, or Firm—James M. Cate

[57] ABSTRACT

A process for propagating a pathogen in a three-dimensional tissue mass cultured at microgravity conditions in a culture vessel containing culture media and a culture matrix is provided. The three-dimensional tissue mass is inoculated with a pathogen and pathogen replication in the cells of the tissue mass achieved.

20 Claims, 3 Drawing Sheets

PATHOGEN PROPAGATION IN CULTURED THREE-DIMENSIONAL TISSUE MASS

This application is a continuation-in-part of U.S. Ser. No. 08/066,292, filed May 25, 1993, now U.S. Pat. No. 5,496,722, which is a continuation-in-part of U.S. Ser. No. 07/939,791, filed Sep. 3, 1992, now U.S. Pat. No. 5,308,764 which is a continuation of U.S. Ser. No. 07/317,921, filed Mar. 2, 1989, now U.S. Pat. No. 5,007,497 which is a continuation-in-part of U.S. Ser. No. 07/317,776, filed Mar. 2, 1989, now U.S. Pat. No. 5,155,034 and is a continuation of U.S. Ser. No. 07/213,558, filed Jun. 30, 1988, now U.S. Pat. No. 5,026,650 and a continuation-in-part of U.S. Ser. No. 07/625,345, filed Dec. 11, 1990, now U.S. Pat. No. 5,153,131.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The invention relates to propagating a pathogen selected from the group consisting essentially of viruses, bacteria, protozoans, parasites, and fungi, by inoculating a three-dimensional tissue mass cultured at microgravity conditions in fluid culture media in a microgravity vessel with the pathogen. The three-dimensional tissue mass may be cultured from normal or abnormal mammalian cells.

BACKGROUND OF THE INVENTION

Cell culture processes have been developed for the growth of single cell bacteria, yeast and molds, which are resistant to environmental stresses or are encased within a tough cell wall. Mammalian cell culture, however, is much more complex because the cells are delicate and cannot withstand excessive turbulent action without sustaining damage. Moreover, mammalian cell cultures require complex nutrient media and environment to support cell proliferation and growth; and it is frequently required that the cells attach themselves to some substrate surface to remain viable and to duplicate. The particular culture requirements of mammalian cells make successful in vitro culturing of both normal and abnormal (for example, carcinomas) mammalian cells difficult to achieve.

There is a lack of adequate in vitro culture systems which produce mammalian tissue of sufficient size and functionality to allow subsequent study of the tissue or study of the effects of specific compounds or organisms on the tissue. Elaborate culture systems for normal and abnormal mammalian cells have been developed in an attempt to grow tissues, however, most do not mimic in vitro conditions and have many limiting aspects.

Normal mammalian tissue has been grown for limited periods of time as two-dimensional monolayers on gelled substrate or other surface for anchoring the cells. Buset et al. "Defining Conditions to Promote the Attachment of Adult Human Colonic Epithelial Cells", *In Vitro Cell. & Dev. Biol.*, Vol. 23. No. 6 pp. 403–412 (June 1987). Colonic cell cultures surviving longer than 7 weeks have been difficult to achieve since crypt cells are unable to survive standard culture regimens, and two-dimensional organ cultures do not support the de novo assembly of stroma and its contribution to epithelial cell growth. Shamsuddin, "Colon Organ Culture as a Model for Carcinogenesis", *Colon Cancer Cells*, Moyer and Poste, Eds. Academic Press, Inc. 1990.

To mimic the in situ environment using monolayer culture, cocultures were prepared using two cell types. A "feeder layer" of fibroblasts or other cells supplied the primary cells with nutrients and other factors difficult to incorporate into a substrate and provided the cellular interaction believed to be necessary for the production of differentiated tissue. Reid et al., "Culturing Hepatocytes and Other Differentiated Cells", *Hepatology*, Vol. 4, No. 3, pp. 548–559 (1984); Haake et al. "Retention of Differentiated Characteristics in Human Fetal Keratinocytes In Vitro", *In Vitro Cell. & Dev. Biol.*, Vol. 25 No. 25 pp. 592–600 (July 1989).

Monolayers "conditioned" with fibroblast cells have been used to impart into the substrate the soluble growth factors for epithelial cells. Kabalin et al. "Clonal Growth of Human Prostatic Epithelial Cells Is Stimulated by Fibroblasts", *The Prostate*, Vol. 14, pp. 251–263 (1989). Monolayers do not produce a three-dimensional tissue, but rather a two-dimensional spread of cells. Often the cells developed by monolayer culture and coculture become undifferentiated and lack normal function.

Three-dimensional in vitro models of differentiated tissue have been produced, however, the cells often do not demonstrate normal cellular activity. Embryonic avian skeletal muscle cells have been grown in vitro on expandable membranes which are gradually and substantially, continuously stretched to simulate the mechanical stimulation of cells experienced in vivo. U.S. Patent No. 4,940,853, Method for Growing Tissue Specimens in Vitro, Vadenburgh, Jul. 10, 1990. The expandable support membrane supports development of three-dimensional structures more closely resemble tissue grown in vivo, however, normal independent cellular activity has not been identified. Additionally, three-dimensional human mammary epithelial cells have been grown in collagen. U.S. Pat. No. 5,026,637, Soule, et al., Jun. 25, 1991. The cells under the disclosed culture conditions did not undergo terminal differentiation and cell senescence, but rather were "immortal" in that they retained the capacity to divide. Thus, normal cellular activity and naturalization was not observed.

A variety of different cells and tissues, such as bone marrow, skin, liver, pancreas, mucosal epithelium, adenocarcinoma and melanoma, have been grown in culture systems to provide three-dimensional growth in the presence of a pre-established stromal support matrix. U.S. Pat. No. 4,963,489, Three-Dimensional Cell and Tissue Culture System, Naughton, et al., Oct. 16, 1990; U.S. Pat. No. 5,032,508, Three-Dimensional Cell and Tissue Culture System, Naughton, et al., Jul. 16, 1991. A biocompatible, non-living material formed into a three-dimensional structure is inoculated with stromal cells. In some cases, the three-dimensional structure is a mesh pre-coated with collagen. Stromal cells and the associated connective tissue proteins naturally secreted by the stromal cells attach to and envelop the three-dimensional structure. The interstitial spaces of the structure become bridged by the stromal cells, which are grown to at least subconfluence prior to inoculating the three-dimensional stromal matrix with tissue-specific cells.

Similar difficulties experienced with normal cell and tissue cultures have been observed with culture systems for propagating abnormal cells and tissues. Although several human carcinoma cell lines have been propagated in vitro, present in vitro culture systems do not permit reproducible cultures of neoplastic cells in large-scale, three-dimensional configuration. The culture of most neoplastic cells has a low success rate, with low percentages of neoplastic cells being established in vitro. Success in cancer therapy can be greatly enhanced using therapeutic testing in models that closely resemble tumorous tissue in vivo and/or in situ.

High-density, three-dimensional in vitro growth of mammalian tumor cells is problematic due to the effects of shear, turbulence, and inadequate oxygenation in conventional cell culture systems. On a small scale, mammalian tumor cells have been grown in containers with small microwells to provide surface anchors for the cells. However, cell culture processes for mammalian cells in such microwell containers generally do not provide sufficient surface area to grow mammalian cells on a sufficiently large scale basis for many commercial or research applications.

Coculture of tumor and normal cells in solid-state culture has been reported as shown in U.S. Pat. No. 4,352,887, Method and Article for Culturing Differentiated Cells, Reid et al., Oct. 5, 1982. However, the three-dimensional environment and culture did not achieve standard clinical testing protocol, such that the three-dimensional environment is nurtured by a mixed-bed of tumor and normal cells.

It is important that tumor models utilized in vitro mimic in vivo properties of tumor cell lines in order that tumor genesis and tumor cell invasiveness can be observed. Although animal models are useful for studying carcinomas, many biochemical and molecular studies require that cells be grown in vitro. Studies on carcinoma cell lines have centered around the expression of oncogenic and protooncogenic markers and nucleotide sequences in order to elucidate the etiology of malignant transformation. Studies have led to insight and speculation as to the origin of transformation, the genetics of transformation, and the treatment or inhibition of the transformation process. However, the models studied have lacked sufficient fidelity for adequate comparison of in vitro culture systems to observations in situ.

Traditional in vitro tumor models have failed to provide intact cell subpopulations, stable isoenzyme patterns, stable ploidy, stable and broad-based growth patterns, and high-fidelity expression of specific cellular proteins. Large scale, high-fidelity three-dimensional in vitro culture carcinoma models are necessary to studying developmental, mutagenic, metastagenic and transformation properties of carcinomas.

The ability to prepare adequate tissue models will provide an in vivo-like environment for propagating pathogens, which frequently cannot be propagated otherwise without great difficulty. For example, viruses are typically intracellular parasites, and cannot be grown in the laboratory unless the growing medium contains living cells.

Generally, little is known about the mechanism by which a viral infection induces certain changes in the activity of the normal functions of the host organism. For example, much of the material collected and known about Norwalk virus has been obtained from studies of infected volunteers because in vitro systems for cultivation of the virus, as with many other viruses, have not yet been devised. Studies with cultured cell explants often result in the Norwalk virus not producing cytopathic changes in the cells.

Norwalk virus plays a significant role in sporadic illness and in outbreaks of acute nonbacterial gastroenteritis. Kaplan, et al., "Epidemiology of Norwalk Gastroenteritis and the Role of Norwalk Virus in Outbreaks of Acute Nonbacterial Gastroenteritis", *Annals of Internal Medicine,* Vol. 96 (Part 1), pp. 756–761 (1982). Norwalk infection produces a brief illness characterized primarily by nausea, vomiting, diarrhea, and abdominal cramps. The acute gastroenteritis produced by Norwalk virus is an extraordinarily common, worldwide disease with a significant public health impact. In the United States, it is second in frequency only to acute viral respiratory disease as a disease occurrence in American families. Dolin, et al., "Novel Agents of Viral Enteritis in Humans", *The Journal of Infectious Diseases,* Vol. 155, No. 3, pp. 365–376 (March 1987). Worldwide, it is estimated that greater than 700 million cases of acute diarrheal disease occur annually in children less than 5 years of age, and such disease may be associated with as many as a 5 million deaths, primarily in developing countries.

Norwalk is a part of the group known as small round structured gastroenteritis viruses (20–30 nm in diameter). Norwalk has a diameter of approximately 27 nm, and has been difficult to successfully propagate in the laboratory. Immunological measurements of susceptibility to Norwalk infection remain unknown because neither humoral nor secretory antibody appears to correlate immunity to infection.

The supply of infectious Norwalk virus material is produced primarily through the production of the disease in volunteers. The infectious material produced provides material for laboratory study of etiologic agents and an experimental host in which important biophysical and immunological properties of etiologic agents can be defined. Blacklow et al., "Acute Infectious Nonbacterial Gastroenteritis: Etiology and Pathogenesis", *Annals of Internal Medicine,* 76:993–1008 (1972). Such studies also provide the opportunity to study the clinical course and pathogenesis of the disease. These methods of studying a virus, however, pose some risk to the infected volunteers.

Various tissue culture procedures for propagating viruses have been proposed, however, most are tedious and time consuming acute infection procedures. Such procedures require multiple passages of cell free virus in tissue culture before an acceptable virus titer is obtained. The infected cell culture is grown to confluency and the grown cells allowed to age. The aged cells are lysed and the virus extracted. The extracted virus can be used to infect a new cell culture.

A variety of cell cultures can be maintained in monolayers on the smooth surface of a solid support, e.g., Petri dishes, glass bottles, or tubes. As soon as such cultures become confluent, forming a united layer of uniform thickness, a virus may be introduced into the liquid medium covering the cells.

Many types of cells can also be grown in suspension, being dispersed within nutrient medium. A virus may then be propagated in the suspended cells. In the conventional system, the fluid medium is decanted off the suspended cells when peak cell concentration is reached. The cells are resuspended in fresh medium which also carries a virus seed. After the period of virus growth, determined by observations of the cytopathic effect of the cells, the harvest is usually passed through a filter and then through a bacterial sterilizing membrane to obtain a solution which contains free viruses released by the disrupted cells.

A disadvantage of large scale suspended cultures of mammalian cells is that air must be sparged through the medium at a high rate and may damage the cells. Further, the sedimentation of the cells is a time-consuming process, and the sedimented cells may be subjected to a medium environment unfavorable in terms of pH and nutritional factors.

The inability to propagate viruses in cell culture frequently necessitates the use of susceptible sub-human primates to grow a particular virus so as to obtain antigen for diagnostic and therapeutic purposes. For example, subhuman primates may be infected with the hepatitis A virus, the infected liver removed, and used to inoculate an in vitro cell culture. U.S. Pat. No. 4,164,566, Hepatitis A Virus Cell Culture in Vitro, Provost et al., Aug. 14, 1979. The cell culture is incubated until hepatitis A antigen is detectable in the culture cells or fluid. Two serial in vitro passages in cell culture are carried out. The hepatitis A virus so modified can be used to prepare live, attenuated hepatitis A vaccine or an inactivated hepatitis A vaccine. Such practices, however, are impractical for commercial use.

Eucaryotic cells have been cultured within a solid carrier body or bed, which is either porous or in a particulate state to provide sufficient internal cavities or space for immobilizing and growing cells and to allow liquid media to pass through the solid carrier and interact with the cells. U.S. Pat. No. 4,203,801, Cell and Virus Culture Systems, Telling, et al., May 20, 1980. The carrier may consist of natural or synthetic materials, such as silicates of diatomaceous earth or polymer particles. A selected cell line is initiated in a monolayer or suspension culture and propagated until the maximum concentration in the cell culture is achieved. The cells are then passed through the bed, whereby the cells are immobilized in the bed. Medium is added to the system and a seed virus introduced. After the cells are disrupted by the virus infection, virus is released and carried away by the medium. Viral material can then be separated from the medium and is available for vaccine formulation or other uses.

Hepatitis A virus has been propagated in human liver tumor cells grown in petri dishes containing nutrient media until the cells reached confluency. U.S. Pat. No. 4,721,675, Production of Hepatitis A Virus in vitro Utilizing a Persistently Virus Infected Cell Culture System, Chan et al., Jan. 26, 1988. The cells were then infected with a single treatment of an inoculum obtained from a human clinical specimen containing the hepatitis A virus. The cell culture system enabled propagating a persistently infected virus producing cell line for passage to other cultures. The system, however, did not mimic in vivo conditions.

U.S. Pat. No. 5,032,508, Three-Dimensional Cell and Tissue Culture System, Naughton, et al., Jul. 16, 1991, discloses a three-dimensional culture system which can be used to culture a variety of different cells and tissues. The tissue cultures grown were proposed for use as a model system for the study of physiologic or pathologic conditions, such as using mucosal epithelium as a model system to study herpes virus or papillomavirus infection. The tissue cultures disclosed by Naughton are initiated using a composite layer taken from a mesenchymal component. Since single cells are not used, it is difficult to define cellular interstitial matrices. The culture system resembles a two-dimensional culture system and it will be difficult to produce the extra-cellular matrix and interstitial components to allow virus cells to translocate from cell to cell.

Difficulties in propagating the Norwalk virus in vitro has precluded the development of commercially available diagnostic assays. A major obstacle to successfully propagating Norwalk virus in vitro is due to the small amount of virus in the stool available for inoculation. Moreover, suitable animal models for the study of these viruses are not available. Relatively little information is available regarding the biophysical and biochemical characteristics of these agents, and for the most part, their significance as etiologic agents of gastroenteritis remains to be established. Understanding of the pathogenesis and immune responses to these agents is at the early stages, and factors responsible for susceptibility of a viral infection remain poorly understood. Since it is difficult to concentrate the virus inoculum, improved cell lines that mimic normal human small intestine tissue would be invaluable for producing larger quantities of virus.

Three-dimensional normal and abnormal cell aggregates and growth achieved in a microgravity vessel provide a unique system in which to simulate the conditions of clinical therapy in vitro. Normal and abnormal mammalian cells cultured in bioreactors, or microgravity vessels, providing low shear and essentially no relative motion of the culture environment with respect to the walls of the culture vessel grow and proliferate to form three-dimensional tissue masses similar to tissues in vitro. Designs for bioreactors which enable such cell and tissue growth are disclosed in U.S. Pat. Nos. 4,988,623, 5,026,650 and 5,153,131.

The three-dimensional tissue masses produced in the bioreactors in vitro permit inoculating the tissue mass with a pathogen to observe the infection produced by the pathogen under conditions closely resembling those in vivo. The culture system provides for proliferation and appropriate cell maturation to form structures analogous to tissue counterparts in vivo. The system enables replicating a pathogen, such as a virus, having biophysical, morphological, immunological, and biological properties characteristic of the pathogen isolated from human sources. The resulting culture may be used to screen cytotoxin compounds and pharmaceutical compounds in vitro, and to produce biologically active molecules in bioreactors. The use of mircrogravity vessels in studying pathogens such as viruses will aid in understanding the pathogenesis by which viral agents cause illness.

The three-dimensional tissues produced from cells taken from different mammalian systems can serve as a model for therapeutic trials directed toward particular pathogens prior to in vivo experimentation. Pathogen therapies, such as radiation, chemotherapy and drugs, can be tested using pathogen infected three-dimensional tissue masses grown under microgravity conditions. For example, the efficacy of anti-viral medications can be tested using virus infected tissue masses grown in microgravity vessels. The development of a means for culturing viruses will enable performing neutralizing antibody studies. Such studies are critical toward the analysis of host short term and long term immune responses to viruses, such as Norwalk. Viral propagation in a three-dimensional tissue mass grown in a microgravity vessel will provide a means by which host immune response to viral infection can be evaluated. Vaccines could then be evaluated for their ability to induce neutralizing responses.

SUMMARY OF THE INVENTION

Pathogens have been propagated in vitro in three-dimensional tissue masses. Mammalian cells were cultured at microgravity conditions in a culture vessel containing culture media and a culture matrix to form a three-dimensional tissue mass. The culture vessel was inoculated with a pathogen and microgravity culture conditions maintained, whereby pathogen replication is achieved in the cells forming the three-dimensional tissue mass. Normal mammalian cells cam be cultured to form a three-dimensional tissue mass. The normal mammalian cells may be selected from the group consisting essentially of epithelial cells, mesenchyme cells, fibroblasts, and mixtures thereof. Abnormal mammalian cells, such as carcinoma cells may also be cultured to form a three-dimensional carcinoma. In the preferred embodiment, the normal mammalian cells are a mixture of small intestine epithelial cells and mesenchyme cells.

The normal mesenchyme cells may be cultured at microgravity conditions for a preselected time prior to adding normal epithelial cells to the culture vessel. Normal mammalian cells may also be cultured at microgravity conditions for a preselected time prior to adding carcinoma cells to the culture vessel. The microgravity culture conditions are created by having a culture vessel in microgravity or by simulating microgravity. Microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The culture media volume may be reduced prior to introducing the pathogen.

The preferred culture media comprises fetal bovine serum and a tri-sugar based medium selected from mixtures of the group consisting of fructose, galactose, and glucose. The preferred culture matrix comprises generally spherical microcarriers.

The pathogen may be selected from the group consisting essentially of viruses, bacteria, protozoans, parasites, and fungi. In the preferred process and embodiment of the invention, the pathogen is Norwalk virus. The three-dimensional tissue mass culture is maintained until tissue cell shedding occurs. The pathogen can be passaged to another cell line under culture conditions. The pathogen products, particularly viral proteins, produced by the process may be used in the development of vaccines or for other purposes. A pathogen inoculum produced from the process may be used for subsequent culture inoculations or for other purposes.

A process for testing the efficacy of a therapeutic agent is also provided. Mammalian cells are cultured at microgravity conditions in a culture vessel containing culture media and a culture matrix until the cells form a three-dimensional tissue mass. The three-dimensional tissue mass is inoculated with a pathogen. The microgravity culture conditions are maintained whereby pathogen replication in the cells forming the three-dimensional tissue mass is achieved. A therapeutic agent is introduced to the culture vessel, and the effect of the therapeutic agent on the pathogen is determined. The therapeutic agent is selected from the group consisting essentially of vaccines, drugs, radiation, and immunotherapeutic agents.

Normal mammalian cells may be selected from the group consisting essentially of epithelial cells, mesenchyme cells, fibroblasts, and mixtures thereof and cultured to form a three-dimensional tissue mass. Abnormal mammalian cells, such as carcinoma cells may also be cultured. The normal mammalian cells may be a mixture of small intestine epithelial cells and mesenchyme cells.

The normal mesenchyme cells may be cultured at microgravity conditions for a preselected time prior to adding normal epithelial cells to the culture vessel. Normal mammalian cells may also be cultured at microgravity conditions for a preselected time prior to adding carcinoma cells to the culture vessel. The microgravity culture conditions are created by having a culture vessel in microgravity or by simulating microgravity. Microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The culture media volume may be reduced prior to introducing the pathogen.

The preferred culture media comprises fetal bovine serum and a tri-sugar based medium selected from mixtures of the group consisting of fructose, galactose, and glucose. The preferred culture matrix comprises generally spherical microcarriers.

The pathogen may be selected from the group consisting essentially of viruses, bacteria, protozoans, parasites, and fungi. The pathogen selected may be Norwalk virus. The three-dimensional tissue mass culture is maintained until tissue cell shedding occurs. The pathogen can be passaged to another cell line under culture conditions.

A process for testing a gene therapy regimen is provided. Mammalian cells are cultured at microgravity conditions in a culture vessel containing culture media and a culture matrix until the cells form a three-dimensional tissue mass. A virus having a desired genome is introduced into the vessel. The microgravity culture conditions are maintained to allow genetic material from the genome of the virus to incorporate into the cells forming the three-dimensional tissue mass. Whether the cells forming the three-dimensional tissue mass contain altered genetic material is determined. The virus may be manipulated to include desired genetic material in its genome.

Normal mammalian cells may be selected from the group consisting essentially of epithelial cells, mesenchyme cells, fibroblasts, and mixtures thereof and cultured to form a three-dimensional tissue mass. Abnormal mammalian cells, such as carcinoma cells may also be cultured. The normal mammalian cells may be a mixture of small intestine epithelial cells and mesenchyme cells. DNA fragments of genetic material may be harvested from the cells of the three-dimensional tissue mass.

The normal mesenchyme cells may be cultured at microgravity conditions for a preselected time prior to adding normal epithelial cells to the culture vessel. Normal mammalian cells may also be cultured at microgravity conditions for a preselected time prior to adding carcinoma cells to the culture vessel. The microgravity culture conditions are created by having a culture vessel in microgravity or by simulating microgravity. Microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The culture media volume may be reduced prior to introducing the virus.

The preferred culture media comprises fetal bovine serum and a tri-sugar based medium selected from mixtures of the group consisting of fructose, galactose, and glucose. The preferred culture matrix comprises generally spherical microcarriers.

DETAILED DESCRIPTION OF THE INVENTION

Figure 1:
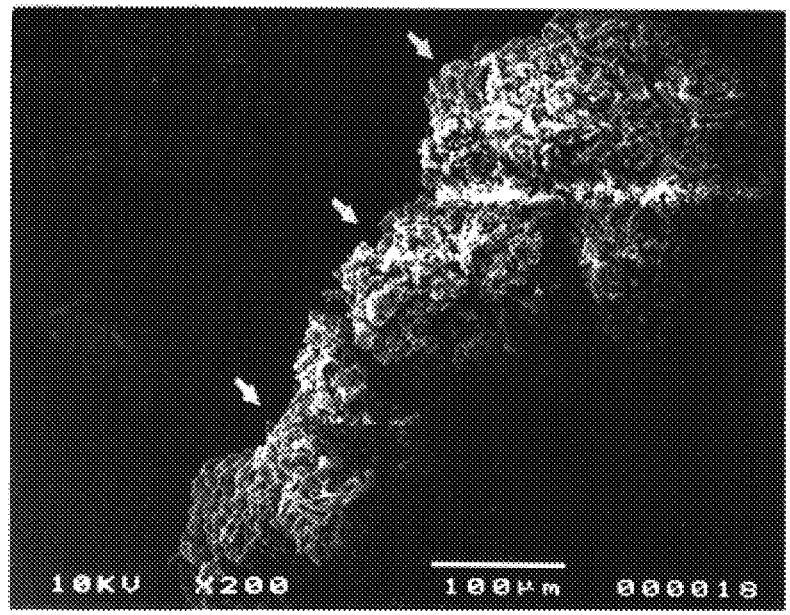
FIG. 1 is a view at 200× magnification of a three dimensional artificial normal organ tissue mass.

The processes and products of the invention are described for both normal and abnormal mammalian tissue used to produce the pathogen and pathogenic products. The following examples are illustrative of the present invention.

In one example, small intestine epithelial and mesenchyme cells were cultured at microgravity conditions to form three-dimensional tissue masses. The microgravity conditions were maintained in a culture vessel containing culture media and a culture matrix. The artificially produced three-dimensional small intestine tissue mass exhibited normal morphology and cell function. After 45–50 days, the three-dimensional small intestine tissue mass was inoculated with Norwalk virus 8FIIa and viral replication achieved. The Norwalk virus was selected for inoculation because it has been traditionally difficult to propagate in in vitro culture. Any virus difficult to culture in vitro using known culturing systems, such as Hepatitis C and HIV and related viruses associated with acquired immune deficiency syndrome may be propagated using the process described herein. Three-dimensional small intestine tissue masses were selected for Norwalk virus infection because the small intestine is the organ in which the virus propagates in situ.

The processes described herein for culturing a three-dimensional small intestine tissue mass may be used to culture tissue masses from cells of other origins, such as blood tissue or structural tissue. The selection of the tissue of cell origin will be dependant upon the pathogen sought to be propagated.

The artificially produced three-dimensional small intestine tissue mass was generated from normal small intestine epithelial and mesenchymal cells. Human small intestine epithelial and mesenchymal cells were obtained from normal organs of patients, predominantly organ transplant donors, showing no evidence of disease. The cells were then propagated in culture.

The cells were initiated and propagated in M3 media supplemented with 2% fetal bovine serum (FBS), designated M3:2, for epithelial cells or with 10% FBS, designated M3:10, for mesenchymal cells. M3 medium is a complex base medium supplemented with many growth factors and nutrients including L-Broth (tryptone broth), bovine pituitary extract, hydrocortisone, essential and non-essential amino acids, pentagastrin, epidermal growth factor, transferrin, selenium, and insulin. Moyer, "Methods for Propagation and Characterization of Human GI and Other Cells for Study of HIV," *J. Tiss. Cult. Meth.,* Vol. 13, pp. 107–116 (1991).

All cell cultures were grown in a Forma humidified $CO_2$ incubator with 95% air, 5% $CO_2$, and constant atmosphere at a temperature of 37° C. Normal mesenchymal cells were passaged as required by enzymatic dissociation with a solution of 0.1% Trypsin, 0.1% EDTA, for 15 minutes at 37° C. After incubation with the appropriate enzymes, the cells were centrifuged at 800×G for 10 minutes in Corning conical 15-ml centrifuge tubes. The cells were then resuspended in fresh medium and diluted into Corning T-flasks with 25 ml of fresh growth medium. Small intestine epithelial cells were passaged by dilution at a 1:2 ratio into fresh M3:2 medium in T-flasks. Cultures of epithelial cells were derived from the ileum and jejunum of three male donors (22–35 years of age). Mesenchymal cells were obtained from the submucosa of five donors (4 males 17–27 years old and a 2-month-old female).

Normal mesenchymal cells were removed from T-75 flasks by enzymatic digestion, washed once with calcium- and magnesium-free phosphate buffer solution (CMF-PBS), and assayed for viability by Trypan Blue dye exclusion (GIBCO). Cells were held on ice in fresh growth medium until inoculation. In the preferred process the primary inoculum introduced into the culture vessel was $2\times10^5$ mesenchymal cells/ml in a 125-ml volume with 5 mg/ml Cytodex-3 micro-carrier beads (Pharmacia, Piscataway, N.J.). Cytodex-3 microcarriers were Type I, collage-coated dextran beads, 175 microns in diameter. After the primary inoculum was prepared for seeding, it was transferred to a culture vessel filled with culture media and cultured at microgravity conditions.

In the preferred process the microgravity conditions were simulated in unit gravity by a horizontal rotating wall vessel (RWV). A preferred RWV bioreactor is described in U.S. Pat. No. 5,026,650 to Schwarz et al. issued Jun. 25, 1991 and is incorporated by reference herein. The rotation of the culture vessel (bioreactor) was controlled to produce the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The trajectory of the cell aggregates was determined. The speed of the rotation of the culture vessel was increased if the cell aggregates fell excessively inward and downward on the downward side of the rotational cycle and excessively outward and insufficiently upward on the upgoing side of the rotational cycle to prevent wall impact. The rotation of the culture vessel was decreased in response to excessive accumulation of tissue aggregation near the outer wall of the culture vessel so as not to restrict three dimensional growth. As the tissue aggregates grow the rotation was adjusted to obtain minimal collision frequency and intensity.

The culture media used in the RWV can be varied. A 1:1 mixture of M3:2 medium and standard minimal essential medium-alpha (MEM-alpha) (GIBCO) supplemented with 10% FBS was used. A preferred media designated GTSF-2 was found to meet the growth requirements of the system without the need for unique growth factors and other complex components found in other media including M3:2. The GTSF-2 media is a trisugar-based medium with glucose, galactose and fructose supplemented with 6% FBS. A preferred formulation for GTSF-2 media is listed in Table 1 below. The pH was adjusted to 7.4 with 1N NaOH.

TABLE 1

Tri-Sugar Based Medium GTSF-2

| Component | Concentration | Source/Order or Designation |
|---|---|---|
| MEM-alpha supplemented with 2.25 gm/L $NaHCO_3$ | 400 ml (40%) | GIBCO/430-1900EB |

TABLE 1-continued Tri-Sugar Based Medium GTSF-2

| Component | Concentration | Source/Order or Designation |
|---|---|---|
| L-15 | 600 ml (60%) | GIBCO/430-1300EB |
| NaHCO$_3$ | 1.35 gm/liter | Sigma/S-5761 |
| HEPES | 3.0 gm/liter | Research Organics/6003H-2 |
| Folic acid | 6.667 µg/liter | Sigma/F-8758 |
| 0.5% Nicotinic acid | 0.667 ml/liter | Sigma/N-4126 |
| Bactopeptone | 0.6 gm/liter | Difco/0118-01 |
| I-inositol | 0.024 gm/liter | Sigma/I-5125 |
| Fructose | 0.13 gm/liter | Sigma/F-3510 |
| Galactose | 0.25 gm/liter | Sigma/G-5388 |
| D-Glucose | 1.0 gm/liter | Sigina/G-5250 |
| 300 mM L-Glutamine | 10 ml/liter | Sigma/G-5763 |
| Gentamycin | 1 ml/liter | GIBCO/600-5750AD |
| Fungizone | 2 ml/liter | GIBCO/600-5295AE |
| Insulin-transferrin-sodium-solenite | 5 ml/liter | Sigma/I-1884 |
| Fetal bovine serum | 60 ml (6%) | Hyclone/A-1111-L |

The primary inoculum of mesenchymal cells was allowed to grow for a minimum of 2–3 days before the medium was changed. Then $2 \times 10^5$ epithelial cells/ml were added prepared as described above for the mesenchymal cells. The organ tissue can be bioengineered to develop desired patterns of cell layering by preselecting the introduction of the epithelial cells into the culture vessel. Also, the cells can be introduced essentially simultaneously into the vessel to produce normal organ tissue.

Culture conditions included mass transfer with exchange of nutrients for metabolic waste and appropriate gas exchange in the culture system. Fresh medium was replenished by 65% of the total vessel volume each 20 to 24 hours. As metabolic requirements increased, fresh medium was supplemented with an additional 100 mg/dl of glucose.

The three-dimensional small intestine tissue mass may be produced in the RWV in both a 1:1 mixture of M3:2 and MEM alpha supplemented with 10% fetal bovine serum (Hyclone Laboratories, Logan, Utah) and tri-sugar based media shown in Table 1 on a preferred culture matrix of 5 mg/ml Cytodex-3 generally spherical microcarriers (Pharmacia, LKB). In alternate embodiments, the tissue mass can be grown in a 1:1 mixture of M3:2 and MEM alpha supplemented with 10% fetal bovine serum (Hyclone Laboratories, Logan, Utah).

The preferred tri-sugar based media was found to meet the growth requirements without the need for multiple growth factors and supplements. The three-dimensional small intestine tissue mass grown in the tri-sugar based media exhibited an epithelial cell component which appeared to proliferate in a more normal fashion. The cultures were not grown to the plateau phase, indicating further capability for continued growth. The artificial tissue did not reach maximum cell densities after 38–45 days of culture.

The tissue masses grew to relatively large sizes as compared to other in vitro methods. After 300 hours of culture, the tissue/microcarrier mass was about 0.2–0.3 cm in size with masses increasing to about 0.4–0.6 cm after approximately 500 hours of culture and over 0.6 cm after 800 hours of culture.

The epithelial cells and mesenchymal cells used to seed the cultures were immunophenotyped and compared to the three-dimensional tissue cultured in the RWV. Samples were harvested at intervals during the culture process for immunocytochemical analysis. The antibodies used to immunochemically characterize the cell types are listed in Table 2 below.

TABLE 2

ANTIBODIES USED FOR IMMUNOCYTOCHEMICAL ANALYSIS

| Antibody Specificity | Dilution | Source/Order No. or Designation |
|---|---|---|
| Pancytokeratin | prediluted | DAKO, Inc. /L1824 |
| Vimentin | prediluted | DAKO, Inc.1L1843 |
| Factor VIII | prediluted | DAKO, Inc./L1809 |
| Villin | 1:20 | Chemicon, Temacria, CA/MAB 1671 |
| Sucrase | 1:20 | A. Elbein, UTHSCSA/YT |
| Angioblasts | 1:20 | Accurate Chem, Westbury, CA/HE3-5/47 |
| Laminin | 1:20 | ICN, Costa Mesa, CA/69-630 |
| Fibronectin | 1:20 | US BIOCH, Cleveland, OH/33752 |
| Proteoglycan | 1:20 | Biological Products for Science, Oxford, UK/MCA 326 |
| Collagen Type IV | 1:20 | DAKO, Inc./M785 |

The keratin, vimentin, and Factor VIII antibodies detect epithelial, fibroblastic, and endothelial cells, respectively. Villin is a cytoskeletal protein only found in epithelial cells from small intestine and colon. The angioblast marker is present in subsets of precursor endothelial cells, particularly dividing cells. Sucrase is an enzyme found in the epithelial cell brush border of the small intestine. Basement membrane and extracellular matrix components laminin, fibronectin, Collagen IV, and proteoglycan were also assayed to determine their expression in the artificially produced three dimensional tissues.

Cultured organ tissue grown on Cytodex-3 microcarriers in the RWV were fixed in OmniFix, an alcohol-based fixative not containing aldehydes or mercury (Xenetics Biochemic, Tustin, Calif.). At all times, extreme care was taken not to damage the delicate artificial tissue comprised of cellular material and microcarrier beads. When an abundance of beads was present, the supernatant fluid was carefully decanted and a sample of beads was enclosed in a biopsy bag, then placed in a cassette to prepare a paraffin block. When bead clusters were scarce, a Shandon Cytoblock Kit (Shandon Inc., Pittsburgh, Pa.) was used.

Cassettes were processed in a standard tissue processor. Five-micron sections were cut from the paraffin-embedded tissues, deparaffinized by standard procedures, then assayed by incubation with the test antibodies (Table 2) followed by use of the universal labeling streptavidin biotin (LSAB) kit (DAKO Inc., Carpenteria, Calif., No. K680), which detects mouse monoclonal and rabbit polyclonal antibodies. The immunocytophenotyping was confirmed by one positive and two negative controls. The positive control was normal tissue sections or normal cells positive for the primary antibody used. The negative controls were 1) PBS only, to test for false binding by "link" antibody and streptavidin, and 2) normal serum of the same species from which the primary antibody was prepared.

Analysis by immunocytochemistry was used to confirm the ability of the seed cells to produce a three-dimensional artificially produced tissue mass with functional epithelial cells and functional mesenchymal cells as well as functional precursor endothelial cells that were not present in the seed culture. As the culture progressed and the tissue mass grew it included functional angioblasts.

Immunophenotyping of the cell types used to seed the coculture in the RWV confirmed the majority of epithelial and mesenchymal cells seeded were keratin and vimentin positive, respectively. In addition, the epithelial cells were at various stages of differentiation. Only a small percentage (<2%) of the cells was positive for Factor VIII, an endothelial cell differentiation marker. Table 3 is a summary of the immunochemical staining reaction of the three dimensional tissue of the present invention. The tissue was harvested at various intervals up to 41 days as noted in Table 3.

An increased percentage $\geq 10\%$ of cells present in the masses consisted of endothelial cells which were Factor VIII positive as confirmed by immunochemistry and growing as patches on the beads. Furthermore, a small percentage, 1–2% of cells, showed de novo expression of the HE3 angioblast antigen which was not present in the seed cultures of mesenchymal cells confirming the presence of angioblasts in the tissue by immunochemistry. Functional cell brush borders were confirmed immunochemically by the presence of sucrase.

Figure 2:
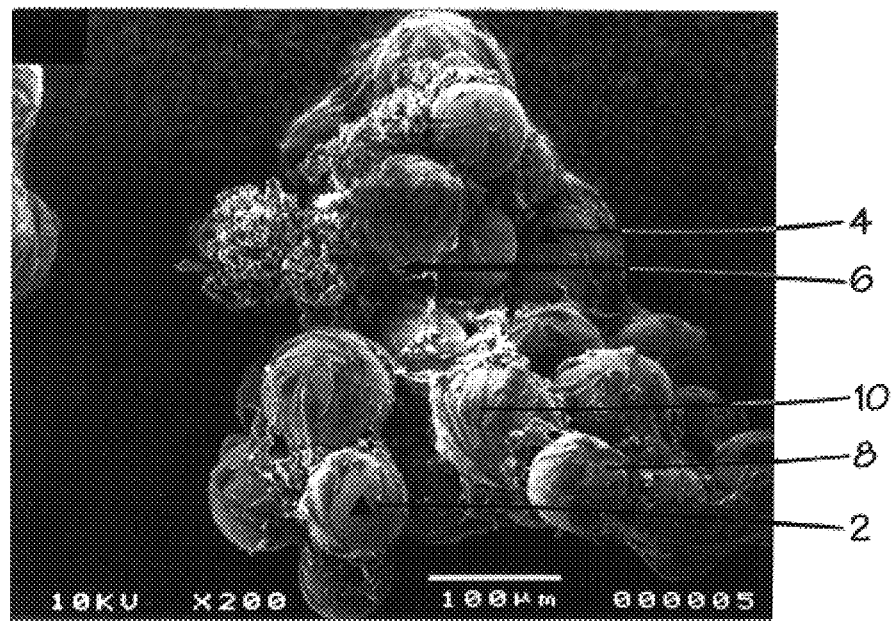
FIG. 2 is a photograph of artificial normal organ tissue at 200× magnification.
Figure 3:
FIG. 3 is a photograph of artificial normal organ tissue at 500× magnification.
Figure 4:
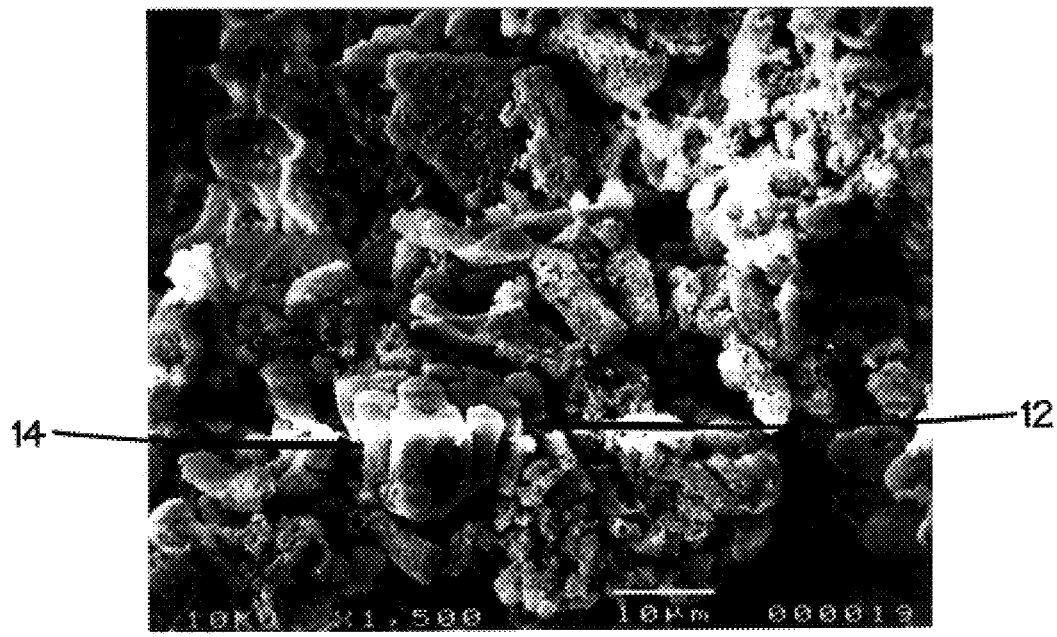
FIG. 4 is a photograph of artificial normal organ tissue at 1500× magnification.
Figure 5:
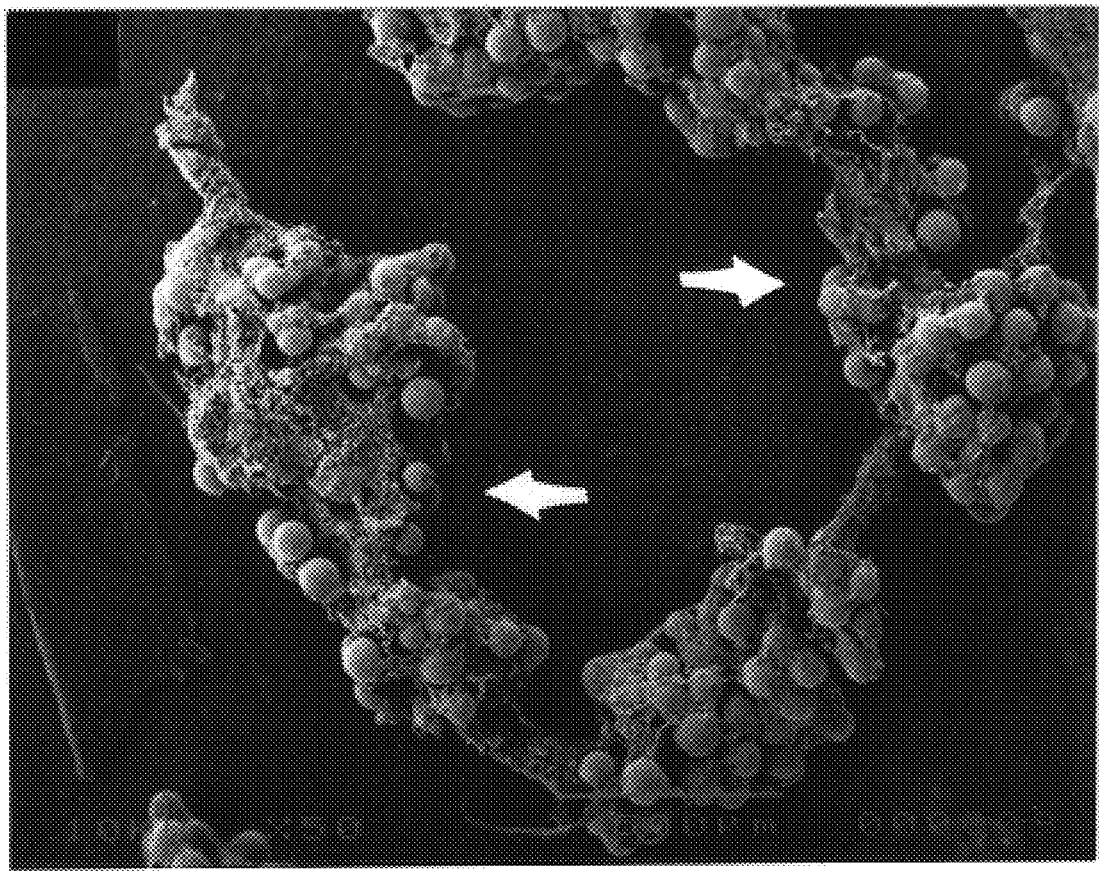
FIG. 5 is a photograph of artificial normal organ tissue at 50× magnification.

FIG. 1 is a photograph of the small intestine artificially produced organ tissue at 200× magnification showing the three dimensional cell aggregate generally indicated by the arrows. FIG. 2 is a photograph of the small intestine organ tissue. The triangular markers at 2 and 4 in the photograph are for reference on the microcarriers. A mass of epithelial cells is shown at 6. Elongated mesenchymal cells are growing on the microcarriers as shown at 8 and 10. FIG. 3 is a higher magnification (500×) of the epithelial mass shown at 6 in FIG. 2. FIG. 4 shows the organized columnar epithelial cells of the small intestine organ tissue at arrows 12 and 14. FIG. 5 shows the three dimensional organ tissue masses joined by cord-like structures of fibroblasts (mesenchymal cells) covered by epithelial cells.

TABLE 3

SUMMARY OF IMMUNOCHEMICAL STAINING ON TISSUE GROWTH IN RWV*

| Antibodies | Specificity or Cell Stained | Days Grown in RWV | | | | |
|---|---|---|---|---|---|---|
| | | 13 | 23 | 25 | 37 | 41 |
| Keratin | Epithelial, Cytoskeletal | +++ | +++ | ++ | ++ | ++ |
| Vimentin | Fibroblasts, some endothelial | +++ | +++ | ++ | ++ | ++ |
| Factor VIII | Endothelial | ++ | +++ | ++ | ++ | ++ |
| Villin | Epithelial, small intestine | + | + | + | + | + |
| HE3 | Angioblasts | – | – | – | ++ | ++ |
| Sucrase | Small intestine, cell brush border | +++ | + | ++ | ++ | ++ |
| Laminin | Basement membrane | + | + | – | + | ++ |
| Fibronectin | Basement membrane | + | + | ++ | ++ | – |
| Proteoglycan | Extracellular matrix | ++++ | ++++ | ++++ | ++++ | ++++ |
| Collagen Type IV | Extracellular matrix | ++ | + | + | ++ | ND |

*Slides were observed and scored on a relative scale as – (negative) to ++++ (maximum staining; very dark positive for >90% of the cells);
+ indicates weaker staining for –25–50% of the cells; ++ indicates moderate staining for greater than 50–75% of the cells.

Samples from the RWV cultures were taken for scanning electron microscopy at the same times as those taken for immunocytochemistry. After removal from the reactor vessels, samples were washed once with CMF-PBS. The samples were suspended in a buffer containing 3% glutaraldehyde and 2% paraformaldehyde in 0.1 M cacodylate buffer at pH 7.4, then rinsed for 5 minutes with cacodylate buffer three times and postfixed with 1% osmium tetroxide (Electron Microscopy Sciences, Fort Washington, Pa.) in cacodylate buffer for 1 hour. Samples were then rinsed for 5 minutes with distilled water three times and then treated for 10 minutes with Millipore (Millipore Corp., Bedford, Mass.) (0.2$\mu$) filtered, saturated solution of thiocarbohydrazide (Electron Microscopy Sciences), then washed for 5 minutes with distilled water five times and fixed with 1% buffered osmium tetroxide for 10 minutes. This last step was necessary to prevent the microcarriers from collapsing.

Samples were then rinsed with distilled water three times and dehydrated with increasing concentrations of EtOH followed by three changes in absolute methanol. After transfer to 1,1,1,3,3,3-hexamethyldisilazane (HMDS) (Electron Microscopy Sciences) samples were allowed to soak for 10 minutes, drained, and air dried overnight. Dried samples were sprinkled with a thin layer of silver paint on a specimen stub, dried, coated by vacuum evaporation with platinum-palladium alloy, and then examined in the JEOL T330 Scanning electron microscope at an accelerating voltage of 5 to 10 kV.

Micrographs taken of 6- to 7-day cocultures showed partial coverage of the microcarriers by normal small intestine mesenchymal cells. Additionally, large developing masses of small intestine epithelium were evident, growing on the microcarrier beadpacks. Samples harvested at approximately 12 days of culture contained small microcarrier packs which were totally engulfed in proliferating small intestine epithelium. Micrographs of samples at 13 days displayed large tissue-like masses that were entirely covered with small intestine epithelium grown on a base layer of mesenchymal cells. Areas of organized columnar epithelium were prominent. As the cultures matured into mid- and late-stage cultures, extremely complex tissue-like masses comprised of mesenchymal and epithelial cells were seen from approximately 16 days of culture until termination at 41 days. These tissues were assembled from smaller masses which were joined by cord-like structures of fibroblasts and covered by epithelial cells several layers deep. In addition, available microcarriers were drawn to the surface of these large masses which were approximately 0.3 to 0.5 cm in diameter. Finally, columnar epithelium was observed to be growing even in the recessed areas of the microcarrier bead packs.

The three-dimensional small intestine tissue mass was grown under the above-described conditions for approximately 45–50 days before the tissue mass was inoculated with Norwalk virus. The rotation of the RWV was stopped and the cells and tissue fragments in culture were allowed to settle by gravity onto the three-dimensional small intestine tissue mass. The volume of the culture media in the RWV was aseptically reduced to approximately 10 ml using a vacuum suction apparatus. The tissue mass was inoculated with 50 $\mu$l of live Norwalk virus 8FIIa inoculum obtained from the Centers for Disease Control (Atlanta, Ga.). The inoculum was added to the vessel and the culture and inoculum gently mixed. The vessel was maintained with the reduced volume of culture media for 1 h at 37° C. in an atmosphere of 5% $CO_2$. In alternate embodiments of the invention, the media volume need not be reduced, or may be reduced by varying amounts.

After 1 h, the growth media volume was replenished to tissue culturing level. Thereafter, the growth media was changed at 24 h intervals for the first four days post infection, and again at days 6 and 8 post infection. The culture media was removed aseptically at each change by vacuum suction. The culture media was decanted off and saved for analysis. The tissue mass fragments remaining after decantation were also saved for analysis. Some cells were fixed in 2% buffered glutaraldehyde, and later embedded in epon blocks for electron microscopic study, and some cells were fixed in buffered 10% formalin, and embedded in paraffin blocks, using standard laboratory procedures. The pathogen culturing conditions were terminated at 8 days post infection. At day 8 post infection cell shedding was extensive.

Virus replication in the cells of the three-dimensional tissue mass was determined using avidin-biotin immunoassay to determine the presence of viral antigen. The formalin fixed and paraffinized tissue culture cells were sectioned for histological evaluation. Additional sections were obtained for immuperoxidase staining procedures with light microscopy. The glutaraldehyde fixed and epon-embedded tissue culture cells were sectioned for inspection by electron microscopy.

Avidin-biotin immunoassay was performed according to standard procedures known to those skilled in the art to detect Norwalk virus antigen. Gary et al., Detection of Norwalk Virus Antibodies and Antigen with a Biotin-Avidin Immunoassay, *J. Clin. Microb.,* Vol 22, No.2:274–278 (August 1985); Johnson et al., Multiple-Challenge Study of Host Susceptibility to Norwalk Gastroenteritis in US Adults, *J. Infect. Diseases,* 161:18–21 (1990), incorporated by reference herein. Each test was performed in quadruplicate. The average of four wells utilizing a capture antibody of high titer of Norwalk virus was compared to the average of four wells utilizing a capture antibody from a volunteer with a low titer of Norwalk antibody obtained prior to experimental infection. Absorbance was read at 470 nm. A positive/negative ratio (P/N) value of greater than 2 was considered positive, and indicative of the presence of Norwalk virus antigen.

The assays were performed twice on samples at undiluted concentrations and twice on samples from 0, 1, 6 and 8 days post infection which had been concentrated 10-fold by gentle vacuum dialysis applied to a 10,000 MW exclusion dialysis membrane. A positive control was run on each microtiter plate.

After two blind testings, positive P/N values of $\geq 3.0$ were repeatedly observed in unconcentrated samples collected at 6 and 8 days post infection. The 10-fold concentrated samples from 1, 6, and 8 days post infection yielded average P/N values of 2.47, 3.72 and 5.35, respectively. Ten-fold concentration of day 0 supernatant (uninfected) yielded only a P/N of 0.01. The results show the generation of Norwalk viral antigens that are reactive in the avidin-biotin immunoassay. A gradual increase of antigen production is suggested with ten-fold concentrates of supernates tested days 2, 6 and 8 post-infection.

Histological evaluation of the infected three-dimensional tissue mass was made based on hematoxylin and eosin-stained sections of tissue harvested at 0, 1, 2, 3, 4, 6 and 8 days post infection. The tissue was devoid of pathology through day 1 post infection. Epithelial and fibroblast nuclei were noted to be swollen beginning at day 2 post infection. Hyperchromatic nuclei and mild degeneration of cytoplasmic and nuclear components were noted by day 3 post infection. Focal nuclear indentations and some inclusion effect were found in cell nuclei at 4 and 6 days post infection. At 8 days post infection, prominent inclusions were found in both epithelial and fibroblast cells. Moderate cytoplasmic and nuclear degeneration appeared at the same time in both cell types. Following viral infection, the parallel cord arrangement of the uninfected fibroblasts degenerated in a progressive manner. These findings suggest a progressive pathologic process such as viral replication.

Glucose utilization rate of the three-dimensional tissue mass in the RWV fell to 4 mg/dl/h at 6 and 8 days post infection, which correlates with the histological evidence of viral infection. Impaired or infected cells would be expected to have lower carbohydrate utilization.

Electron microscopy performed with infected three-dimensional small intestinal tissue mass from 0, 6, and 8 days post infection revealed that mitochondrial swelling and loss of cytoplasmic integrity had occurred starting at day 6 post infection. Nuclear alterations were also noted on day 8 post infection. Cytoplasmic integrity had been lost in cells at day 8 post infection. The results confirmed the histological evidence of infection.

Immunohistological staining of Norwalk-infected formalin fixed and paraffinized tissue from the RWV was also performed. Acute and convalescent ($\geq 23$ weeks after illness) paired sera from four of Norwalk-challenged volunteer donors were used for the immunohistological studies. The sera were selected on the basis of their avidin-biotin solid-phase reactivity to Norwalk virus. Acute reciprocal titers were $\leq 100$ versus convalescent titers of $\geq 6400$. The acute and convalescent sera was used to stain the virus-infected three-dimensional small intestine tissue.

Immunoperoxidase staining procedures known to those skilled in the art, such as the avidin-biotin complex (ABC) immunoperoxidase staining procedure described by Burk et al., Detection of non-A, non-B, hepatitis antigen by immunocytochemical staining, *Proc. Natl. Acad. Sci.,* 81:3195–3199 (1984), incorporated by reference herein, may be used to ascertain the replication of Norwalk virus in infected tissues or tissue culture cells. The paired donor sera were used as the primary antibody source on serial sections of tissue from the RWV. The sera was adsorbed first with rabbit liver powder in order to eliminate nonspecific background reactivity. Biotinylated goat anti-human IgG was used as the second antibody, followed by avidin-biotinylated horseradish peroxidase complex. The electron donor 3-3' diaminobenzidine-$(HCI)_4$ was used in the presence of $H_2O_2$.

The acute sera reacted with uninfected tissues at a low background level. The intensity of the stain increased several fold when identical tissue sections were reacted with convalescent sera from the same volunteer. Immunostaining indicated that the nuclei of the cells were the predominant site of the antibody deposition.

No paired sera reacted with uninfected tissues from the RWV. The acute sera from one volunteer exhibited a low level of reactivity with RWV tissue obtained at day 8 post infection. Serial sections from tissue were stained by the convalescent sera more intensely and with a greater number of cells. Another series of sections from Day 6 post infection stained with acute or convalescent sera from a second volunteer showed the intensity of the stain to be greater with convalescent serum.

Densitometer measurement of stained nuclei in photomicrograph slides showed convalescent serum from two volunteers was 1.53 and 3.47 times darker than that stained acute serum. These immunochemical results indicate that Norwalk virus can be propagated in the normal three-dimensional small intestine tissue mass grown in the RWV.

Passage of 6 and 8 post infection virus into human embryonic lung fibroblasts resulted in baseline positive levels of Norwalk virus antigen, as detected by avidin-biotin immunoassay, being observed after several weeks of culture.

This provided further indication that Norwalk virus was successfully propagated in the RWV-grown tissue and RWV conditions. The three-dimensional tissue mass virus propagating system allows the replication a virus having biophysical, morphological, immunological, and biological properties characteristic of Norwalk virus isolated from human sources.

Normal three-dimensional tissue masses grown under the microgravity conditions of the RWV provide a model for successfully propagating pathogens in a normally active tissue having normal functions. The three-dimensional tissue masses grown under microgravity conditions will provide a model for studying the propagation and mechanisms by which pathogens function, and allow the development of treatments for infectious and noninfectious pathogens.

In particular, classical virus treatment dictates that large quantities of a virus be grown for inactivation or attenuation and vaccination or multiple passages in order to develop a viral vaccine. The three-dimensional tissue mass provides a high-fidelity tissue model necessary to maintaining viral fidelity. Propagating viruses in three-dimensional tissue masses and associated extra-cellular matrices and interstitial components will provide insight into the mechanism by which a virus infects a cell, and the effects in relation to promoters, growth factors, and cell type. The process by which a virus incorporates nucleotide sequences into the host genome or utilizes the host biosynthetic capabilities to replicate can also be studied. Critical pathways for viral replication and the temporal sequence involved in replication may be observed as well. Other factors that may be studied utilizing the present invention include identifying the mechanisms and cell types involved in viral shedding, and tracking the pathway by which the shed virus is transmitted to other hosts.

The three-dimensional tissue mass may be infected with a virus to achieve viral replication and thereby, antibody production, and an avenue to vaccine production. Large quantities of virus with high-fidelity envelope and protein content will facilitate vaccine development and understanding of disease processes. Viral products, particularly proteins, are required in large amounts for vaccine development. The culture model described herein provides a means for propagating large quantities of previously difficult to culture viruses. The culture model will assist in inferring the immunological mechanisms utilized to combat the infection.

Propagating and growing viruses in cultured three-dimensional tissue masses as provided may result in a virus that can be subsequently propagated in large quantities in two-dimensional culture. Viruses are highly adaptive mechanisms because they attach to the genome of a host. The viruses grown in the artificially produced three-dimensional tissue mass are adapted to the synthetic environment of the cultured tissue and the cells of the tissue. It is likely that a virus which propagates in the three-dimensional tissue described herein will also propagate under two-dimension culture conditions. Thus, it will be possible to passage a virus propagated in the three-dimensional tissue mass to a two-dimensional culture. Adapting viruses which are difficult to culture in vitro to successfully propagate and grow in two-dimensional culture will enable the production of the large quantities of virus and viral product needed to develop vaccines and to perform research concerning such viruses.

In addition to propagating pathogens in the three-dimensional tissue mass, the tissue, once infected, will allow the testing of the efficacy of therapeutic agents. The effect of therapeutic agents, such as vaccines, drugs, and radiation, on a pathogen infecting the host tissue can be tested prior to administering the agent to a patient. Immunotherapeutic or chemotherapeutic treatments to alleviate or eradicate diseases ranging from cancer and infections with high morbidity and mortality through more benign maladies, such as rhinitis, may be developed.

A virus propagated in the normal three-dimensional tissue mass may also be premodulated to carry desired genetic information which will incorporate into the host cell DNA. Gene therapy regimens may be defined by first culturing mammalian cells from a selected organ as described. A virus specific to the cells of the selected organ which has been encoded or manipulated to possess desired genetic material may be transfected into the cells of the three-dimensional tissue mass. It can then be determined whether the desired genetic material is incorporated into the genome of the host cells, thus replacing a particular genetic deficiency. Moreover, a virus possessing the ability to produce a desired physiological effect my be transfected into the cells of the three-dimensional tissue mass. The three-dimensional tissue mass will provide a model for determining whether desired physiological effects will be obtained prior to attempting such therapy on animals and humans.

In an alternate process and embodiment of the present invention, three-dimensional tissue masses grown from abnormal cells may be used to propagate pathogens. For example, aggregates of human urogenital tract carcinoma cells may be cultured in vitro to produce artificial high-fidelity three-dimensional carcinomas. The artificially-produced carcinoma masses exhibit intact cell subpopulations of differentiated and undifferentiated cells, stable isoenzyme patterns, stable ploidy, stable and broad-based cell growth patterns, high-fidelity expression of specific cellular proteins, specifically proteoglycan, and specific protein markers, such as Prostate Specific Antigen (PSA) and Prostatic Acid Phosphatase (PAP).

In an embodiment of the invention utilizing artificially-produced high-fidelity three-dimensional human carcinomas, the carcinomas may be propagated from carcinoma cells obtained from a carcinoma of selected origin. Carcinoma cells may also be obtained directly from the organ of carcinoma origin, or the organ of metastases. The carcinomas may be infected with a pathogen to obtain the results described herein for normal three-dimensional tissue masses. It would be desirable to infect abnormal tissue masses with pathogens because of the rapid proliferation of cells generally observed with cancerous tissues. Abnormal three-dimensional tissue masses grown in a RWV may provide accelerated and increased production of pathogenic compounds when infected. Abnormal tissue masses may exhibit some confounding of proteins produced as compared to normal tissue, however, confounding factors can be checked against pathogen production in normal three-dimensional tissue masses.

Methods for growing high-fidelity human urogenital tract carcinomas in RWV culture are provided. Any carcinoma cell line, however, may be grown according to the methods provided. Carcinoma cells may be cocultured with normal human cells, such as normal fibroblasts established from primary cultures from the normal cells of organ donors. In an alternate embodiment of the invention, the carcinoma cells may be cultured without the presence of normal fibroblasts. It is preferred that the fibroblasts selected be specific to the organ of interest.

Human prostate carcinoma cell lines designated PC3 and LnCap by convention and primarily undifferentiated prostate carcinoma cell lines were obtained from American Type Culture Collection (ATCC, Rockville, Md.). The PC3 cells were ATCC no. CRL-1435 and the LnCap were ATCC no. CRL-1740. Both cell lines were successfully propagated according to the methods described herein. The normal cells selected were normal adult prostate fibroblasts established from primary cultures from the normal prostate of organ donors. The normal fibroblasts were obtained from Clonetics Corporation (San Diego, Calif.).

The prostate carcinoma cells and normal prostate fibroblasts were initiated and propagated separately in T-flasks containing a preferred culture media designated GTSF-2. A preferred formulation for GTSF-2 media is provided in Table 1 below.

The carcinoma cells and the fibroblasts were grown in monolayer culture. GTSF-2 was found to meet the growth requirements of the monolayer cultures, and the subsequent culture vessel system, without the need for unique growth factors and other complex components found in other media. The GTSF-2 media is a tri-sugar-based medium containing the sugars: glucose, galactose and fructose supplemented with 7% fetal bovine serum (FBS). The pH of the media was adjusted to 7.4 with 1N NaOH.

TABLE 1

Tri-Sugar Based Medium GTSF-2

| Component | Concentration | Source/Order or Designation |
|---|---|---|
| MEM-alpha supplemented with 2.25 gm/L NaHCO$_3$ | 400 ml (40%) | GIBCO/430-1900EB |
| L-15 | 600 ml (60%) | GIBCO/430-1300EB |
| NaHCO$_3$ | 1.35 gm/liter | Sigma/S-5761 |
| HEPES | 3.0 gm/liter | Research Organics/6003H-2 |
| Folic acid | 6.667 µg/liter | Sigma/F-8758 |
| 0.05% Nicotinic acid | 0.667 ml/liter | Sigma/N-4126 |
| Bactopeptone | 0.6 g/liter | Difco/0118-01 |
| I-Inositol | 0.024 g/liter | Sigma/I-5125 |
| Fructose | 0.13 g/liter | Sigma/F-3510 |
| Galactose | 0.25 g/liter | Sigma/G-5388 |
| D-Glucose | 1.0 g/liter | Sigina/G-5250 |
| 300 mM L-Glutamine | 10 ml/liter | Sigma/G-5763 |
| Gentamycin | 1 ml/liter | GIBCO/600-5750AD |
| Fungizone | 2 ml/liter | GIBCO/600-5295AE |
| Insulin-transferrin-sodium-solenite | 5 ml/liter | Sigma/I-1884 |
| Fetal bovine serum | 70 ml (7%) | Hyclone/A-1111-L |

The monolayer cell cultures were maintained in a humidified $CO_2$ Forma incubator in 5% $CO_2$:95% air constant atmosphere, and 98% humidity at a temperature of 37° C. When glucose in the cell culture media was depleted to 20–60 mg/dl, 50 to 100% of the culture media was replaced. Cell cultures were expanded when cells became confluent on the bottom of the T-flasks. Standard enzymatic dissociation with a solution of 0.1% Trypsin, 0.1% EDTA, in phosphate-buffered saline (PBS) solution for 15 minutes at 37° C., was used to separate the cells.

Once the concentration of normal and carcinoma cells grown in monolayer culture was sufficient to provide the desired cell concentration for seeding into the culture vessel, the carcinoma cells and the normal fibroblasts were removed from the T-flasks. The cells were removed by enzymatic digestion with 0.1% Trypsin, 0.1% EDTA, for 15 minutes at 37° C., and washed once with calcium- and magnesium-free PBS (CMF-PBS). The cells were assayed for viability using Trypan Blue stain exclusion (GIBCO). The cells were centrifuged at 800×G for 10 minutes in conical 15-ml centrifuge tubes in GTSF-2 with 7% FBS. The cells were then resuspended in fresh medium and diluted into Corning T-flasks with 25 ml of fresh growth medium. Cells were held on ice in fresh growth medium until inoculation into a culturing vessel (RWV). The carcinoma cells and the normal fibroblasts cells were kept separate during preinoculation procedures.

In the preferred method for culturing the cells, the primary inoculum of monodispersed normal cells introduced into the culture vessel was $4 \times 10^5$ normal prostate fibroblast cells/ml in the 110-ml volume vessel, with 5 mg/ml (550 mg total) Cytodex-3 microcarrier beads (Pharmacia, Piscataway, N.J.). Cytodex-3 microcarriers were Type I, collagen-coated dextran beads, 175 microns in diameter. After the primary inoculum was prepared for seeding, it was transferred to a culture vessel filled with GTSF-2 with 7% FBS culture media and cultured at microgravity conditions. Rotation speed in the vessel was initially set at a rate of 12–14 rpm.

In an alternate embodiment, a primary inoculum of the monodispersed prostate carcinoma cells was introduced into the culture vessel at $2 \times 10^5$ cells/ml in the 110 ml volume with 5 mg/ml Cytodex-3 micro-carrier beads, as described above.

In another embodiment, a primary inoculum of monodispersed normal cells may be introduced into the culture vessel at $4 \times 10^5$ normal prostate fibroblast cells/ml with an inoculum of $2 \times 10^5$ prostate carcinoma cells/ml with 5 mg/ml Cytodex-3 microcarrier beads described above. Thereby, a coculture of prostate carcinoma cells and normal prostate fibroblasts will be present in the vessel at the initiation of culturing in the RWV. The RWV has been previously described herein. Rotation of the vessel was controlled as previously described herein.

Culture conditions included mass transfer with exchange of nutrients for metabolic waste and appropriate gas exchange in the culture system. The culture medium was changed in response to glucose depletion. Fresh medium was replenished by 50% of the total vessel volume each 20 to 24 hours.

Within 48 hours of inoculation, the preferred primary inoculum of monodispersed normal human prostate fibroblasts formed visible three-dimensional cellular aggregates. The fibroblast aggregates were maintained in solution through rotation of the RWV at 25 rpm. The fibroblasts were allowed to become confluent such that the beads were entirely covered before a coculture inoculum of $2 \times 10^5$ prostate carcinoma cells/ml was added to the culture vessel, resulting in a coculture of prostate carcinoma cells and normal cells. Although normal prostate fibroblasts were selected as the primary inoculum in the preferred embodiment, normal prostate mesenchymal cells, initiated and propagated as described herein for normal fibroblasts, may form the primary inoculum, inoculated at $4 \times 10^5$ normal mesenchyme cells/ml.

The coculture process described allows carcinoma tissues to be engineered, or constructed, through the control of culture conditions and the introduction of cells. Tissue engineering of carcinoma growth enables the manipulation of the results of the culture system by introducing various carcinoma cell types into the culture system at different points during the culturing process to obtain the desired cellular growth and aggregate size.

Alternately, the monodispersed carcinoma cells formed visible cellular aggregates at approximately 72 hours post inoculation. The prostate cell aggregates were maintained through rotation of the RWV at 25 rpm. The prostate cell aggregates were maintained as a monoculture of prostate carcinoma cells. This culturing process also allows carcinoma tissues to be engineered, or constructed, through the control of culture conditions and the introduction of cells.

In both embodiments, cells were allowed to grow until the aggregates exceeded 4 mm in diameter (approximately 11 to 15 days) with minimal necrosis. When the aggregates reached the desired size, viable cell samples were harvested over periods of 3 to 4 days, and prepared for the following discussed analyses. Higher cell densities were observed with cocultured carcinoma cells than with the carcinoma cells cultured alone. Under the microgravity conditions, the carcinoma and normal cells were observed to express morphological and biochemical characteristics found in carcinoma cells in situ, and achieved three-dimensional cellular aggregates of up to 5 mm in diameter.

The assessment of fidelity of the carcinoma cell aggregates was based upon the regulation of specific oncogene markers and protein markers. The assessment of fidelity relates to the in situ environment. Morphological and biochemical characteristics of the aggregates were observed using scanning electron microscopy and histology. Samples from RWV cultures were taken at multiple time points throughout the course of the culturing procedures for histologic analysis (approximately 72 hours post inoculation and then every 72 hours). Standard immunostaining procedures, including antibodies specific to vimentin, keratin, and cytokeratin, were also utilized to evaluate differentiation and the presence of cellular components. All procedures used to assess the fidelity of the carcinoma cell aggregates are known to those skilled in the art.

Results of staining showed the cocultured and cultured prostate carcinoma cell aggregates to exhibit intact cell subpopulations of differentiated and undifferentiated cells. Cellular structures, such as microvilli, were observed. The cellular protein, proteoglycan, was specifically identified in the cells of the three-dimensional aggregates. Protein markers, Prostate Specific Antigen (PSA) and Prostatic Acid Phosphatase (PAP), were observed in the prostate carcinoma cell aggregates.

Samples from the RWV cultures were taken for scanning electron microscopy at the same time as those taken for histological analysis. Micrographs taken of 3 to 5 day cultures showed substantial coverage of the microcarriers by three-dimensional prostate carcinoma cell aggregates. Microcarriers were uniformly covered with cell aggregates by 11 to 15 days of culturing in the vessel.

A cDNA library created from cocultured prostate carcinoma cells cultured in T-flasks and a cDNA library created from cocultured prostate carcinoma cells cultured in a rotating wall vessel were used in a subtractive hybridization process to identify mRNA of specific expressions associated with the particular culture environment. Oncogenic markers known to be specific for the cell types studied were analyzed by the method of Pardee and Lang for isolation of mRNA. The subtractive hybridization process used to create the cDNA libraries is a standard, commercially available technology (Invitrogen). A C-has/bas-1 probe was used to assess specific mRNA expression.

By separation of mRNA and DNA, basic patterns of isoenzymes were observed and determined to be stable. Protein markers, PSA and PAP, which are specific markers for prostate tumors, were expressed. Stable ploidy was also demonstrated. The oncogene markers and protein markers form a basis for assessing fidelity and comparing transitions from models grown in T-flasks to the high-fidelity three-dimensional cultures grown as cocultures and monocultures in the RWV.

A cDNA library was also created for the monocultured cell aggregates cultured in T-flasks and a library created for monocultured cells cultured in the rotating wall vessel using the same technology described for the cocultured cell culture cDNA libraries. Similar results at the cellular and molecular level were observed.

The assessment of carcinoma cell aggregate fidelity may also be based upon the ability of the aggregates to withstand successful transplantation into nude mouse models. The cocultured and monocultured prostate carcinoma cell aggregates will provide high-fidelity three-dimensional prostate carcinoma masses providing tumor models that closely resemble the carcinoma in situ.

Artificially-produced human bladder carcinomas have also been propagated from carcinoma cells obtained from a human bladder carcinoma. The bladder carcinoma cell line propagated, designated T-24 by convention, is a primarily undifferentiated human bladder carcinoma cell line. The T-24 cell line is a mixed-bed carcinoma having a mixture of standard T-24 cell subpopulations. The bladder carcinoma cells were obtained from ATCC no. HTB 4. In the preferred embodiment of the inventive process, carcinoma cells were cocultured with normal human cells. The normal human cells were normal human bladder fibroblasts established from primary cultures from the normal bladders of organ donors. The normal human bladder fibroblast cell line was also obtained from Clonetics.

The same procedures and techniques described herein with reference to the culturing of human prostate carcinoma cells were followed to prepare high-fidelity three-dimensional human bladder carcinoma cell aggregates resembling carcinomas found in situ. Bladder carcinoma cells were cocultured or monocultured as described. Following culturing, the bladder carcinoma cell aggregates were analyzed as described above for prostate carcinomas. Similar characteristics of intact cell subpopulations of differentiated and undifferentiated cells, stable isoenzyme patterns, stable ploidy, stable and broad-based cell growth patterns and high-fidelity expression of specific cellular proteins, specifically proteoglycan, were observed with the bladder carcinoma cell aggregates as with the prostate carcinoma cells. The cocultured and monocultured human bladder carcinoma cell aggregates were found to be high-fidelity three-dimensional bladder carcinoma masses that provide tumor models that closely resemble the bladder carcinoma in situ.

The high-fidelity three-dimensional carcinomas grown in the RWV may be inoculated with a virus or other pathogen for obtaining the advantages discussed above with normal three-dimensional tissue masses. Because abnormal, particularly carcinoma or cancerous, cells are immortal and rapidly proliferating, there is a great number of cells continually available to provide hosts for a virus. Abnormal mammalian cells grown into three-dimensional tissue masses will provide an environment for producing large quantities of a virus and viral products.

Propagating pathogens in cultured high-fidelity three-dimensional carcinomas, as with normal three-dimensional tissue masses, will provide a means for assessing the therapeutic value of a drug or other treatment. Utilizing the three-dimensional tissue masses for propagating pathogens will remove the psychological effects on a patient of taking or being exposed to a therapeutic agent, and the observer error when monitoring such treatments for likelihood of being successful as a therapy. All therapy assessments may be made under in vitro conditions which closely resemble in situ. Moreover, it could be used to formulate patient specific treatments and therapies.

In addition to viruses, other pathogens normally found undesirable in traditional tissue culture, such as bacteria and pleomorphic gram-negative non-motile mycoplasmas, are included in the pathogens that may be cultured in three-dimensional tissue masses. Thus, the apparatus and method of the present invention are effective for replicating a broad spectrum of pathogens, including viruses, bacteria, and intermediate organisms such as mycoplasmas.

The examples included are not intended to limit the scope of the present invention. Other substitutions, modifications and variations of the process for propagating pathogens are apparent to those skilled in the art without departing from the disclosure and scope of the invention.

What is claimed is:

1. A process for propagating a pathogen comprising the steps of:
   a) culturing mammalian cells at microgravity conditions in a culture vessel containing culture media and a culture matrix capable of culturing the cells at microgravity culture conditions until the cells form a three-dimensional tissue mass;
   b) inoculating the culture vessel with a pathogen; and
   c) maintaining the microgravity culture conditions whereby pathogen replication is achieved in the cells forming the three-dimensional tissue mass.

2. The process for propagating a pathogen of claim 1, wherein the mammalian cells are normal mammalian cells.

3. The process for propagating a pathogen of claim 1, wherein the mammalian cells are normal mammalian cells selected from the group consisting essentially of epithelial cells, mesenchyme cells, fibroblasts, and mixtures thereof.

4. The process for propagating a pathogen of claims 1, wherein the mammalian cells are abnormal mammalian cells.

5. The process for propagating a pathogen of claim 1, wherein the mammalian cells are carcinoma cells.

6. The process for propagating a pathogen of claim 1, wherein the mammalian cells are a mixture of small intestine epithelial cells and mesenchyme cells.

7. The process for propagating a pathogen of claim 1, wherein the normal mammalian cells are selected from the group consisting essentially of organ tissue cells, structural tissue cells, blood tissue cells, and mixtures thereof.

8. The process for propagating a pathogen of claim 1, wherein step (a) further comprises culturing normal mesenchyme cells at microgravity conditions for a preselected time prior to adding normal epithelial cells to the culture vessel.

9. The process for propagating a pathogen of claim 1, wherein step (a) further comprises culturing normal mammalian cells at microgravity conditions for a preselected time prior to adding carcinoma cells to the culture vessel.

10. The process for propagating a pathogen of claim 1, wherein microgravity culture conditions are created by having a culture vessel in microgravity.

11. The process for propagating a pathogen of claim 1, wherein microgravity culture conditions are created by simulating microgravity.

12. The process for propagating a pathogen of claim 1, wherein microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel.

13. The process for propagating a pathogen of claim 1, wherein the culture media comprises fetal bovine serum and a tri-sugar based medium selected from mixtures of the group consisting of fructose, galactose, and glucose.

14. The process for propagating a pathogen of claim 1, wherein the culture matrix comprises generally spherical microcarriers.

15. The process for propagating a pathogen of claim 1, wherein the pathogen is selected from the group consisting essentially of viruses, bacteria, protozoans, parasites, and fungi.

16. The process for propagating a pathogen of claim 1, wherein the pathogen is Norwalk virus.

17. The process for propagating a pathogen of claim 1, wherein step (b) further comprises reducing the culture media volume prior to introducing the pathogen.

18. The process for propagating a pathogen of claim 1, wherein the three-dimensional tissue mass is maintained until tissue cell shedding occurs.

19. The process for propagating a pathogen of claim 1, wherein the pathogen replicated in the culture vessel can be passaged to a cell line under different culture conditions.

20. The process for propagating a pathogen of claim 1, wherein the pathogen infects the three-dimensional tissue mass.

* * * * *